(12) United States Patent
Ashida

(10) Patent No.: US 11,249,087 B2
(45) Date of Patent: Feb. 15, 2022

(54) DEVICE FOR MONITORING EFFECTIVE STATE OF KETOGENIC DIET

(71) Applicant: MEIJI CO., LTD., Tokyo (JP)

(72) Inventor: Kinya Ashida, Tokyo (JP)

(73) Assignee: MEIJI CO., LTD., Tokyo (JP)

(*) Notice: Subject to any disclaimer, the term of this patent is extended or adjusted under 35 U.S.C. 154(b) by 136 days.

(21) Appl. No.: 16/494,864

(22) PCT Filed: Apr. 6, 2018

(86) PCT No.: PCT/JP2018/014673
§ 371 (c)(1),
(2) Date: Sep. 17, 2019

(87) PCT Pub. No.: WO2018/186481
PCT Pub. Date: Oct. 11, 2018

(65) Prior Publication Data
US 2020/0088735 A1 Mar. 19, 2020

(30) Foreign Application Priority Data

Apr. 6, 2017 (JP) .............................. JP2017-076201
Aug. 25, 2017 (JP) .............................. JP2017-162775

(51) Int. Cl.
*G01N 33/64* (2006.01)
*G01N 33/497* (2006.01)

(52) U.S. Cl.
CPC .......... *G01N 33/64* (2013.01); *G01N 33/497* (2013.01); *Y10T 436/202499* (2015.01); *Y10T 436/25875* (2015.01)

(58) Field of Classification Search
CPC ............ G01N 33/497; G01N 33/4975; G01N 33/4977; G01N 33/64; Y10T 436/200833; Y10T 436/202499; Y10T 436/25875
(Continued)

(56) References Cited

U.S. PATENT DOCUMENTS 4,114,422 A * 9/1978 Hutson .................. G01N 30/02
436/130
4,931,404 A * 6/1990 Kundu .................. G01N 33/64
422/413

(Continued)

FOREIGN PATENT DOCUMENTS

| JP | 2003-79601 | 3/2003 |
| JP | 2016-514725 | 5/2016 |
| WO | 2017/038101 | 3/2017 |

OTHER PUBLICATIONS

Alkedeh et al. Biosensors, vol. 11, 26, Jan. 19, 2021, pp. 1-16.*
(Continued)

*Primary Examiner* — Maureen Wallenhorst
(74) *Attorney, Agent, or Firm* — Wenderoth, Lind & Ponack, L.L.P.

(57) ABSTRACT

The purpose of the present invention is to provide a ketogenic diet monitoring device for managing the effective state of a ketogenic diet for an animal individually. The ketogenic diet monitoring device of the present invention has a configuration in which the amount of metabolite in gases carried from the inside to the outside of the body of an animal for which the effective state of a ketogenic diet is being managed is measured once and/or a plurality of times over time and monitored.

1 Claim, 4 Drawing Sheets

(58) Field of Classification Search
USPC .............. 436/20, 128, 130, 181; 422/83, 84
See application file for complete search history.

(56) References Cited

U.S. PATENT DOCUMENTS

| | | | |
|---|---|---|---|
| 5,071,769 A * | 12/1991 | Kundu | A61B 5/4872 436/128 |
| 9,183,757 B2 * | 11/2015 | Yamada | G09B 19/0092 |
| 10,509,025 B2 * | 12/2019 | Kodama | G01N 33/497 |
| 2014/0350105 A1 | 11/2014 | D'Agostino et al. | |
| 2016/0078782 A1 * | 3/2016 | Meidenbauer | G16H 20/60 434/127 |
| 2017/0332951 A1 | 11/2017 | Ahmad et al. | |
| 2018/0214410 A1 | 8/2018 | Hagihara et al. | |

OTHER PUBLICATIONS

International Search Report dated Jul. 10, 2018 in International Application No. PCT/JP2018/014673.
Neri, et al., "Design and Development of a Breath Acetone MOS Sensor for Ketogenic Diets Control", IEEE Sensors Journal, 2010, vol. 10, No. 1, pp. 131-136.

* cited by examiner

DEVICE FOR MONITORING EFFECTIVE STATE OF KETOGENIC DIET

TECHNICAL FIELD

The present invention relates to a monitoring device used for managing the effective state of a ketogenic diet.

BACKGROUND ART

Previously, based on the assumption that a ketogenic diet or a high fat diet (in particular, a carbohydrate-restricted high fat diet) would provide a therapeutic method for terminal cancer patients, the effectiveness of a ketogenic diet with respect to Japanese terminal lung cancer patients was examined. As a result, it has been discovered that unexpectedly significant treatment of the cancer is possible and the QOL can be improved by a ketogenic diet, such as compositions for treating cancer including a carbohydrate-restricted high fat diet or a combination thereof, wherein, preferably, fat is not less than 120 g, and/or carbohydrate is limited to not more than 30 g per day, and/or the daily caloric ingestion is not less than 20 kcal/kg body weight, and/or a medium chain fatty acid oil (MCT oil) or the like is combined (Patent Literature 1).

It is also known that a ketogenic diet is effective in improving cerebral function and for prevention and treatment of cognitive dysfunction (Patent Literature 2). In addition, it is known that a ketogenic diet has an effect on obesity, cardiovascular disorder, type 2 diabetes, epilepsy, acne, cancer, polycystic ovary syndrome, neurological disorder, Alzheimer's disease, Parkinson's disease, and head injury (Non Patent Literature 1).

In the past, during the course of intensive research conducted to provide an agent for food or an agent for medicine for suppressing an increase in the amount of gastric emptying and for delaying gastric emptying, a method has been discovered by which the amount of amino acid being metabolized is measured noninvasively using exhaled air as a sample, by monitoring the discharged amount of exhaled air of 13CO2 from an animal fed with various amino acids labeled with 13C (Patent Literature 3).

It is generally known that a ketogenic diet ingested by an animal is metabolized in the body of the animal, and some results in acetone and is discharged out of the body of the animal in the form of exhaled air or gases carried out of the body through the skin or mucosa.

Known methods for measuring acetone in gases include those using a multi-function exhaled air analyzer (Patent Literature 4) and an exhaled air measurement device (Patent Literature 5).

A system for estimating a diabetic indicator value using the amount of exhaled acetone is also known (Patent Literature 6).

Citation List

Patent Literature

Patent Literature 1: WO 2017/038101 A
Patent Literature 2: WO 2016/013617 A
Patent Literature 3: JP 5938219 B
Patent Literature 4: JP 5921562 B
Patent Literature 5: JP 5139186 B
Patent Literature 6: JP 2015-102381 A

Non Patent Literature

Non Patent Literature 1: European Journal of Clinical Nutrition (2013) 67, 789-796

SUMMARY OF INVENTION

Technical Problem

So far, no monitoring device has been known that measures the amount of metabolite in gases (exhaled air and evaporation from the skin or mucosa) carried out of the body of an animal, to manage the effective state of a ketogenic diet of the animal. Furthermore, no monitoring device has been known that measures the amount of acetone in gases carried out of the body of an animal for the purpose of managing the effective state of a ketogenic diet while the ketogenic diet is being ingested, or managing the effective state of a ketogenic diet for a patient and/or a pre-patient of a disorder against which an ingestion of a ketogenic diet is effective; or as a method for assisting the ingestion of a ketogenic diet meal or for screening or determining whether the physical condition or physical constitution is such that a ketogenic diet can be metabolized effectively as a ketone body source.

It has been contemplated that if, with respect to the management of the effective state of a ketogenic diet for an animal, the amount of acetone in gases carried out of the body can be measured noninvasively and instantaneously or continuously, for example, and if thereby the metabolizing state of the ketogenic diet as a ketone body source for the animal can be monitored, it would become possible to manage the effective state of the ketogenic diet individually. Thus, development of such device has been a problem.

Solution to Problem

Intensive efforts made by the present inventors have led to a device for measuring and monitoring, once and/or a plurality of times over time, the amount of acetone in gases carried from the inside to the outside of the body of an animal, and a method of using the same, resulting in the present invention.

The present invention provides the following inventions.

[1] A monitoring device for measuring, once and/or a plurality of times, an amount of acetone in a gas carried out of the body of an animal to manage an effective state of a ketogenic diet.

[2] A monitoring device for managing the effective state of a ketogenic diet according to [1], wherein that performs measurement once and/or a plurality of times to manage an effective state of a ketogenic diet, wherein the animal according to [1] is a patient and/or a pre-patient of a disorder against which an ingestion of the ketogenic diet is effective.

[3] A monitoring device for managing the effective state of a ketogenic diet according to [1], wherein the measurement is performed once and/or a plurality of times to manage ingestion of the ketogenic diet in accordance with metabolism in the body of the animal before and after ingestion of the ketogenic diet.

[4] A monitoring device for managing the effective state of the ketogenic diet according to [1], wherein the measurement is performed once and/or a plurality of times for screening for the suitability of a subject with respect to maintenance or improvement of the effective state of the ketogenic diet.

A ketogenic diet monitoring device of the present invention for monitoring an effectiveness of a ketogenic diet includes: an ingestion information acquisition unit for acquiring information about an amount of ingestion of a ketogenic diet ingested into the body of an animal; an acetone concentration measurement unit for measuring acetone concentration that is an amount of acetone in a gas carried from the inside to the outside of the body of the animal; and a determination unit which, based on the information about the amount of ingestion of the ketogenic diet acquired by the ingestion information acquisition unit and the acetone concentration information measured by the acetone concentration measurement unit, determines a state of metabolizing of the ketogenic diet by the animal.

Preferably, the determination unit performs the determining based on an increase or decrease in the acetone concentration before and after ingestion of the ketogenic diet. Preferably, the determination unit, if the acetone concentration indicates an increasing tendency compared to before the ingestion of the ketogenic diet, determines a state in which the animal is metabolizing the ketogenic diet as a ketone body source, or that the animal has a physical condition or a physical constitution capable of metabolizing the ketogenic diet as a ketone body source.

Advantageous Effects of Invention

According to the present invention, it is possible to provide a device that measures and monitors the amount of metabolite in gases carried from the inside to the outside of the body of an animal once and/or a plurality of times over time, and a method of using the same. With the monitoring device and the method of using the same according to the present invention, it is possible to perform: management of the effective state of a ketogenic diet while the ketogenic diet is being ingested; management of the effective state of a ketogenic diet for a patient and/or a pre-patient of a disorder against which an ingestion of the ketogenic diet is effective; and screening or judgement, as a method of assisting the ingestion of a ketogenic diet meal, as to whether the physical condition or the physical constitution is such that the ketogenic diet can be metabolized effectively as a ketone body source.

According to the present invention, it is possible to provide a device that measures and monitors, once and/or a plurality of times over time, the amount of acetone in gases carried from the inside to the outside of the body of an animal when a ketogenic diet is caused to be ingested, and a method of using the same.

According to the present invention, it is possible to provide a device that measures and monitors the amount of acetone, once and/or a plurality of times over time, in gases carried out of the body of a patient and/or a pre-patient of a disorder against which an ingestion of a ketogenic diet is effective, and a method of using the same.

According to a monitoring device of the present invention, it is possible to measure the amount of metabolite in gases (exhaled air, evaporation from the skin or mucosa) carried out of the body of an animal, and to manage the effective state of a ketogenic diet of the animal.

According to a monitoring device of the present invention, it is possible to measure the amount of metabolite in gases (exhaled air, evaporation from the skin or mucosa) carried out of the body of an animal when a ketogenic diet is caused to be ingested, and to manage the effective state of the ketogenic diet of the animal.

According to a monitoring device of the present invention, it is possible to measure, for a patient and/or a pre-patient of a disorder against which an ingestion of a ketogenic diet is effective, the amount of acetone in gases carried out of the body of an animal, and, in view of the rate of metabolism of the ketone diet as a ketone body source, to perform meal management, such as adjusting the balance between carbohydrates and fat in the meal. It is sometimes difficult to ingest a large amount of a ketogenic diet depending on tastes due to preferences.

According to the present invention, it is possible, by adjusting the ingestion while performing monitoring, to provide only an appropriate amount of feeding as a necessary and sufficient amount, and to avoid excessive ingestion of a non-preferred ketogenic diet. The present invention also provides the advantage that, by adjusting the ingestion of a ketogenic diet while performing monitoring (thereby clarifying an amount of feeding of the ketogenic diet effective for maintaining or improving physical condition), it becomes possible for an animal (particularly a human) that feeds to feed consciously or unconsciously.

According to a monitoring device of the present invention, it is possible to measure the amount of acetone in gases carried out of the body of an animal and perform screening or judgement as to whether the physical condition or physical constitution is such that a ketogenic diet can be metabolized effectively as a ketone body source.

Additional features related to the present invention will become apparent from the following description and the attached drawings. Other objects, features, and effects will become apparent in light of the following detailed description of embodiments.

DESCRIPTION OF EMBODIMENTS

Figure 1:
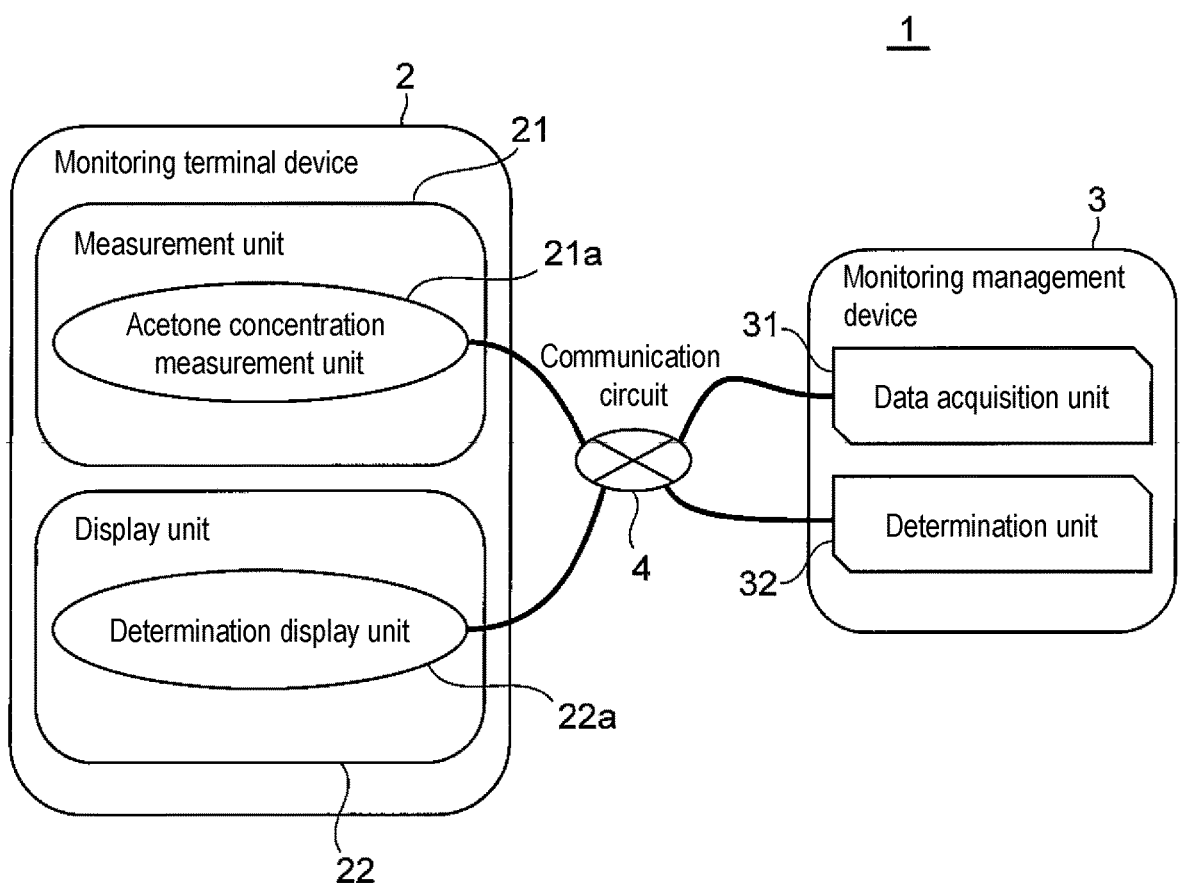
FIG. 1 is a functional block diagram illustrating an example of a monitoring device according to an embodiment.

In the following, preferable embodiments of the present invention will be described. However, the present invention is not limited to any of the individual aspects which will be described below.

In the present invention, arbitrary mammals may be used. Examples include: rodents such as mice, rats, hamsters, and guinea pigs; lagomorphs such as rabbits; ungulates such as pigs, cattle, goats, horses, and sheep; carnivorans such as dogs and cats; and primates such as humans, monkeys, rhesus monkeys, cynomolgus monkeys, marmosets, orangutans, and chimpanzees. The mammals are preferably rodents (such as mice) or primates (such as humans), more preferably primates, and even more preferably humans.

In the present invention, the effective state of a ketogenic diet refers to a state in which the animal is ingesting a ketogenic diet from outside the body and is effectively utilizing the ketogenic diet for the maintenance of the life of the animal or for the life activities of the animal. The effective state of a ketogenic diet can be determined from a state in which the ketogenic diet is being metabolized effectively as a ketone body source. For example, the effective state can be determined from the state of the amount of acetone in gases (exhaled air and evaporation from the skin or mucosa) carried from the inside to the outside of the body of the animal. The amount of acetone in the gases (exhaled air and evaporation from the skin or mucosa) carried from the inside to the outside of the body of an animal may be managed in terms of absolute amount and/or relative amount. The amount of acetone in gases (exhaled air and evaporation from the skin or mucosa) carried from the inside to the outside of the body of an animal varies individually from one animal to another. Accordingly, a judgement may be made based on a rise, a decrease and/or an increase and the like in the amount of acetone between a period in which a ketogenic diet is not ingested and a period in which the ketogenic diet is ingested, or before and after ingestion of the ketogenic diet for the same individual. If a constant increasing tendency is observed compared to before the ingestion of the ketogenic diet, it can be determined that an effect has been obtained. Preferably, the increasing tendency indicates a statistically significant difference, for example.

If, for the same individual, the difference in the amount of acetone is in a constant state between the period in which the ketogenic diet is not ingested and the period in which the ketogenic diet is ingested, or between before and after ingestion of the ketogenic diet, it can be determined that the effect is maintained and preferable.

In the present invention, the management of the effective state of a ketogenic diet refers to identifying the state in which the ketogenic diet is being metabolized effectively as a ketone body source, and seeking to maintain and/or improve the physical condition of the animal within a target range.

In the present invention, a ketogenic diet refers to a meal or food with which it is possible to produce ketone bodies in the living body of the animal. Examples include a high fat diet, a medium chain fatty acid diet, and a food in which a ketone body ester or a ketogenic amino acid are formulated. In the present invention, these ketogenic diets may be referred to as a ketone body source diet.

In particular, ketogenic diets or a combination thereof for treating cancer include a ketogenic diet, such as a high fat diet (so-called "carbohydrate-restricted high fat diet"), for example. Examples of the gases carried out of the body of a cancer patient include exhaled air and gases carried out of the body through the skin or mucosa.

In the present invention, the animal for which the effective state of a ketogenic diet is managed may include a patient and/or a pre-patient of a disorder against which an ingestion of a ketogenic diet is effective. In the present invention, examples of the disorder against which an ingestion of a ketogenic diet is effective include obesity, cardiovascular disorder disorders, type 2 diabetes, epilepsy, acne, cancers, polycystic ovary syndrome, neurological disorders, Alzheimer's disease, Parkinson's disease, and head injury.

In the present invention, a patient of a disorder against which an ingestion of a ketogenic diet is effective refers to those diagnosed with the disorder. A pre-patient refers to those diagnosed with a potential for the disorder or exhibiting predisposition for and/or early signs of the disorder. The pre-patient includes those who are genetically susceptible to the disorder and/or those who wish by their own will for ingestion of a ketogenic diet to prevent the disorder.

In the present invention, to determine the amount of ingestion of a ketogenic diet before and after ingestion of the ketogenic diet, monitoring may be performed using a device of the present invention. In addition, monitoring may be performed by a device of the present invention to perform screening or judgement as to whether the physical condition or physical constitution of the animal for which the effective state of a ketogenic diet is being managed is such that, after ingesting the ketogenic diet, the ketogenic diet can be metabolized effectively as a ketone body source.

Figure 2:
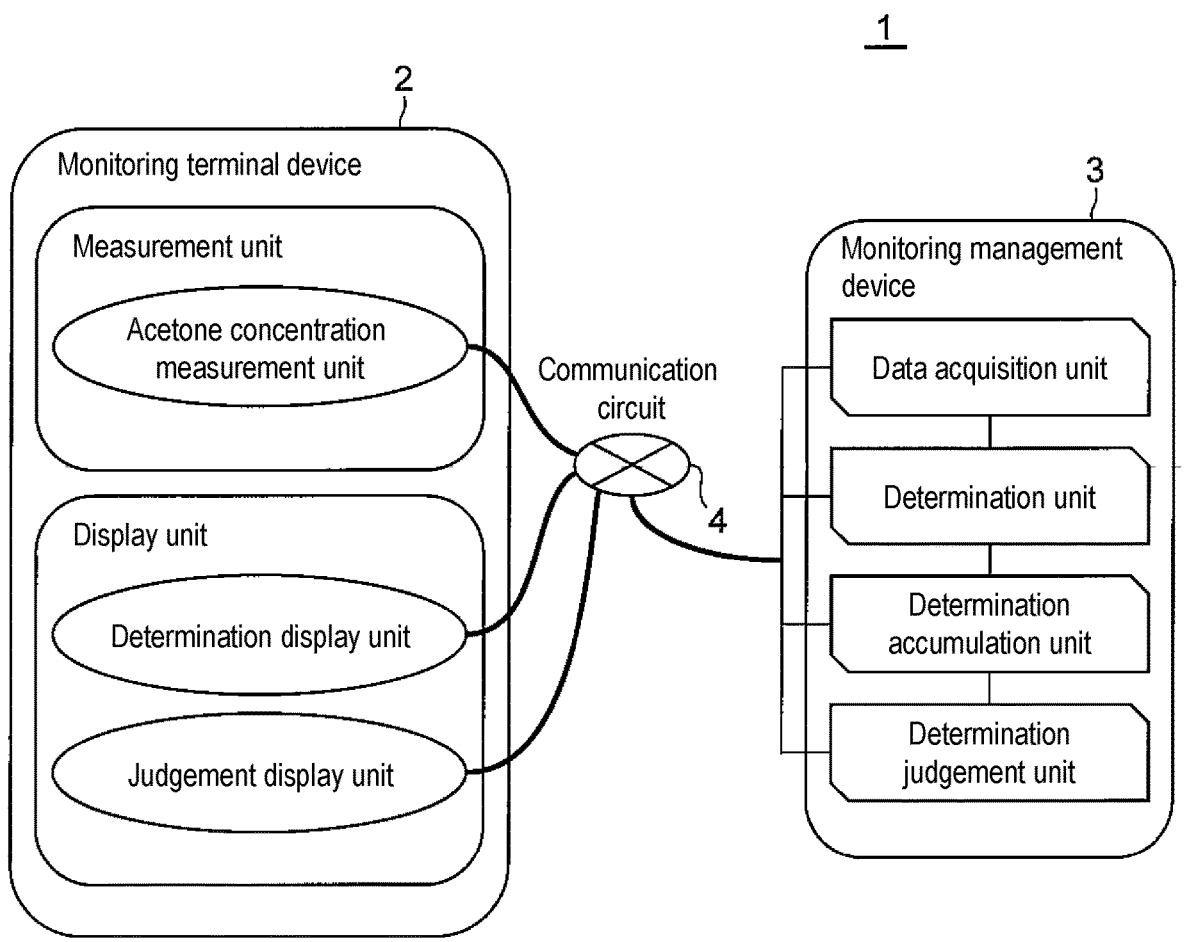
FIG. 2 is a functional block diagram illustrating an example of a monitoring device according to an embodiment.

FIG. 1 and FIG. 2 depict functional block diagrams illustrating examples of a monitoring device according to embodiments.

The monitoring device 1, as depicted in FIG. 1, for example, is provided with a monitoring terminal device 2 and a monitoring management device 3. The monitoring terminal device 2 and the monitoring management device 3 are connected via a communication circuit 4, and are able to perform transmission and reception of information between each other. The monitoring terminal device 2 includes a measurement unit 21 including an acetone concentration measurement unit 21a, and a display unit 22 including a determination display unit 22a. The monitoring management device 3 includes a data acquisition unit 31 and a determination unit 32.

The acetone concentration measurement unit 21a of the monitoring terminal device 2 measures an acetone concentration that is the amount of acetone in gases carried from the inside to the outside of the body of an animal. The determination display unit 22a displays the result of determination made by the determination unit 32 of the monitoring management device 3.

The data acquisition unit 31 of the monitoring management device 3 acquires ketogenic diet ingestion information, acetone concentration information, and individual information of the animal that ingests the ketogenic diet. The ketogenic diet ingestion information includes information about the amount of ingestion of a ketogenic diet being ingested into the body of the animal, and may further include information about at least one of the time of ingestion, period of ingestion, and type of the ketogenic diet, for example. The individual information of the animal may include information about at least one of the type, age, sex, physical size, physical condition, physical constitution, and disease name, for example, of the animal.

The ketogenic diet ingestion information and the individual information of the animal are input to the data acquisition unit 31 from an input means, not illustrated, with which the monitoring terminal device 2 or the monitoring management device 3 is provided, for example. That is, the data acquisition unit 31, as an ingestion information acquisition unit, acquires the ketogenic diet ingestion information. The acetone concentration information is acquired from the acetone concentration measurement unit 21a.

The determination unit 32 determines the state of metabolizing of the ketogenic diet by the animal, based on the ketogenic diet ingestion information and the acetone concentration information. The determination unit 32 determines whether the ketogenic diet is being metabolized effectively as a ketone body source, i.e., whether ketone bodies are being produced in the body of the animal. The determination unit 32 determines the metabolizing state based on an increase or decrease in acetone concentration before and after ingestion of the ketogenic diet, for example. The determination unit 32, if the acetone concentration after ingestion of the ketogenic diet indicates an increasing tendency compared to before ingestion, determines the state in which the animal is metabolizing the ketogenic diet effectively as a ketone body source, or that the animal has a physical condition or a physical constitution capable of metabolizing the ketogenic diet effectively as a ketone body source.

The determination unit 32 calculates the rate of increase in acetone concentration due to ingestion of the ketogenic diet, based on a ketogenic diet ingestion amount (g) per body weight (Kg) of the animal and the difference in acetone concentration before and after ingestion of the ketogenic diet. If, compared to a reference value set in advance, the reference value is exceeded, the acetone concentration is indicative of an increasing tendency. Accordingly, it is determined that the state is such that the ketogenic diet is being metabolized effectively as a ketone body source, or that the animal has a physical condition or a physical constitution capable of metabolizing the ketogenic diet effectively as a ketone body source. On the other hand, if the reference value is not exceeded, the acetone concentration is not indicative of an increasing tendency. Accordingly, it is judged that: the state is such that the ketogenic diet is not being metabolized effectively as a ketone body source; or that the physical condition or physical constitution of the animal is not capable of metabolizing the ketogenic diet effectively as a ketone body source. It may also be determined to which of a plurality of metabolizing levels (levels 1 to 5) with gradually set ranges the rate of increase in acetone concentration belongs, for example.

The reference value or the metabolizing level ranges may be corrected based on the individual information of the animal. For example, in the case of an animal with a large physical size, such as an adult male, correction may be made in a direction for increasing the reference value. In the case of an animal with a small physical size, such as an adult female or a child, correction may be made in a direction for decreasing the reference value.

The result of determination made by the determination unit 32 is displayed on the determination display unit 22a of the monitoring terminal device 2. Accordingly, it can be recognized, by looking at the determination display unit 22a, whether the ingestion of the ketogenic diet is effective for the animal. The correction may be made based on published information, such as statistics information published by administrative organs; published papers; and conference presentations, or non-published information based on independently accumulated data. The correction may be made artificially using artificial intelligence (AI) functionality or the like.

According to the monitoring device 1 having the configuration described above, it is possible to decide on an ingestion amount of the ketogenic diet from the next time, based on the result of the determination. It is also possible to judge whether the animal has a physical condition or a physical constitution capable of metabolizing the ketogenic diet effectively as a ketone body source. By keeping records continuously, it also becomes possible to identify a change in the physical condition or physical constitution of the animal.

According to the monitoring device 1, it is possible, for a patient and/or a pre-patient of a disorder against which an ingestion of a ketogenic diet is effective, to adjust ingestion while performing monitoring using the device 1, despite the fact that it is sometimes difficult, depending on tastes due to preferences, to ingest a large amount of a ketogenic diet, which enables meal management, such as adjusting the balance between carbohydrates and fat in the meal. Accordingly, it becomes possible to provide only an appropriate amount of feeding as a necessary and sufficient amount, and to avoid excessive ingestion of a non-preferred ketogenic diet. According to the monitoring device 1, the amount of feeding of a ketogenic diet effective for maintaining or improving physical condition becomes clear. Thus, the monitoring device 1 provides the effect of allowing the animal (human, in particular) that feeds to feed consciously or unconsciously.

The monitoring device 1 may be a device in which the determination unit 32 for displaying the determination according to the measurement result and the determination display unit 22a for displaying the determination are connected directly for monitoring at one location. The monitoring device 1 may be a device (FIG. 1) in which the monitoring terminal device 2 including the measurement unit 21 and the determination display unit 22a is connected, via the communication circuit 4, with the monitoring management device 3 including the data acquisition unit 31 handling data and the determination unit 32 for determining the effective state of ketogenic diet. Examples of the communication circuit 4 include radio waves, various known wireless communication lines, and wired communication lines. The monitoring may be performed in real-time or at certain time intervals. The monitoring may be performed at one location or a plurality of locations, such as the patient himself or herself, the doctor, a nurse, a laboratory technician, a dietician, a management facility, and a ketogenic diet manufacturer.

The monitoring device 1 may be configured from: a monitoring terminal device including a measurement unit, a determination display unit, and a judgement display unit for receiving and displaying a judgement; and a monitoring management device (FIG. 2) including a data acquisition unit, a determination unit, a determination accumulation unit for accumulating the determination, and a determination judgement unit for making a judgement based on the accumulated determination.

The monitoring terminal device may be similar in shape to a wristwatch or eye glasses, or may be in any shape or form suitable for wearing, such as an accessory or a belt. The monitoring terminal device may include a monitoring management server for managing a plurality of monitoring terminal devices in conjunction with one another. The monitoring management server may be used to decide on a generally optimized amount of treatment from the treatment results with respect to a plurality of patients.

As the monitoring terminal device or the monitoring management device, any digital computers including personal computers and supercomputers may be used. Cell phones, smartphones, tablets, alarm devices and the like may also be used.

Figure 3:
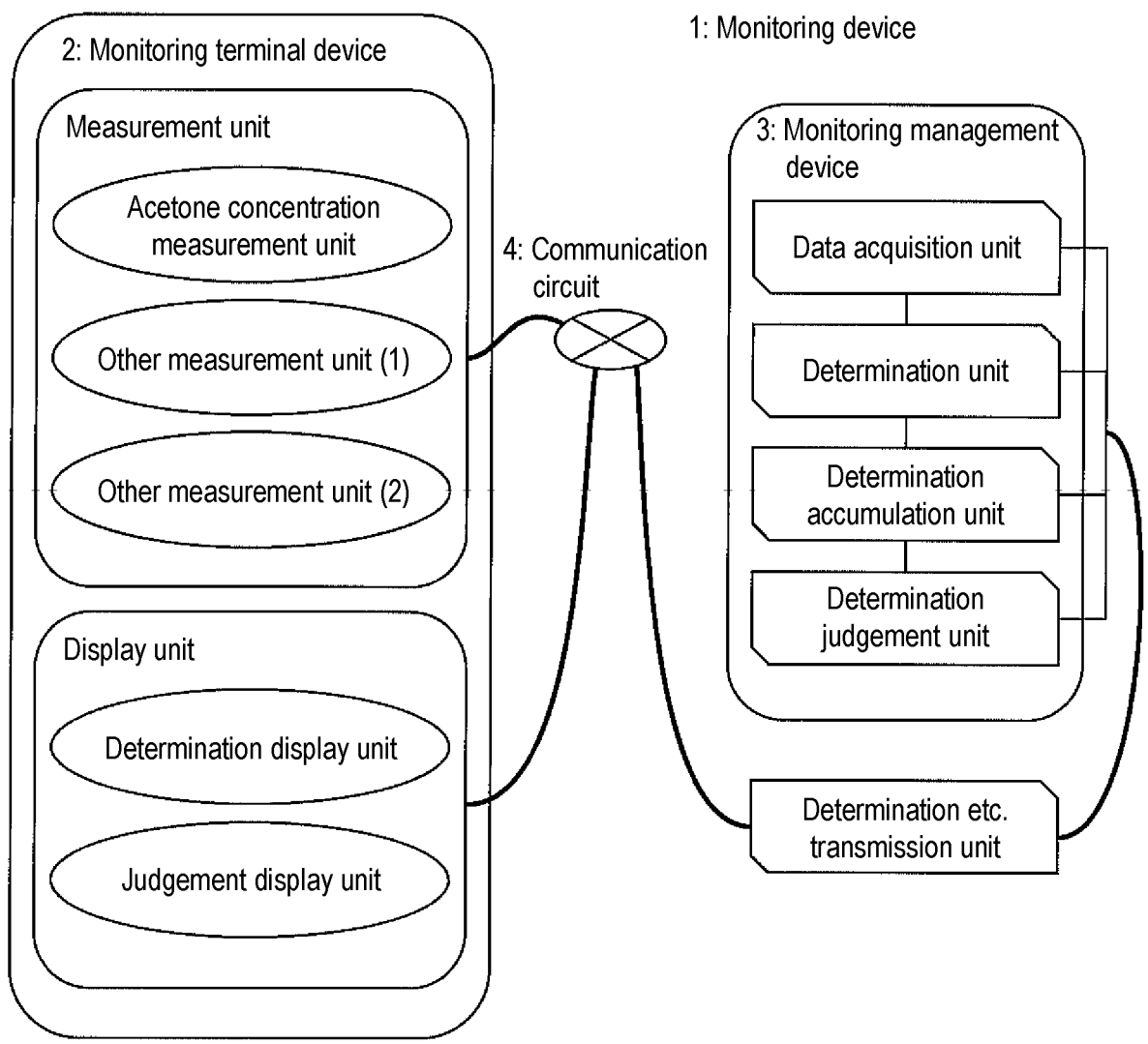
FIG. 3 is a functional block diagram illustrating an overall configuration of a monitoring device according to an embodiment.

FIG. 3 is a functional block diagram illustrating an overall configuration of the monitoring device according to an embodiment.

The monitoring terminal device 2 includes an acetone concentration measurement unit for measuring acetone concentration, and a display unit for displaying data from a determination etc. transmission unit. The display unit includes a determination display unit. A determination display unit for displaying data from the determination etc. transmission unit may also be included. Further, one or a plurality of other measurement units useful for managing the effective state of ketogenic diet may also be included.

The monitoring management device 3 includes a data acquisition unit for acquiring measurement data, a recording unit for recording measurement data, and a determination unit for determining, from the data, the amount of ketone body source diet that has been metabolized. A determination accumulation unit for accumulating determinations, and a determination judgement unit which, from the accumulated determinations, adjusts the amount of feeding of a meal and the amount of fat and performs screening or makes a judgement as to the suitability of a ketogenic diet may also be included. A determination from the determination unit and a judgement from the determination judgement unit are sent via the determination etc. transmission unit to the determination display unit or the judgement display unit and displayed on the monitoring terminal device. The monitoring management device may include a data recording unit.

Figure 4:
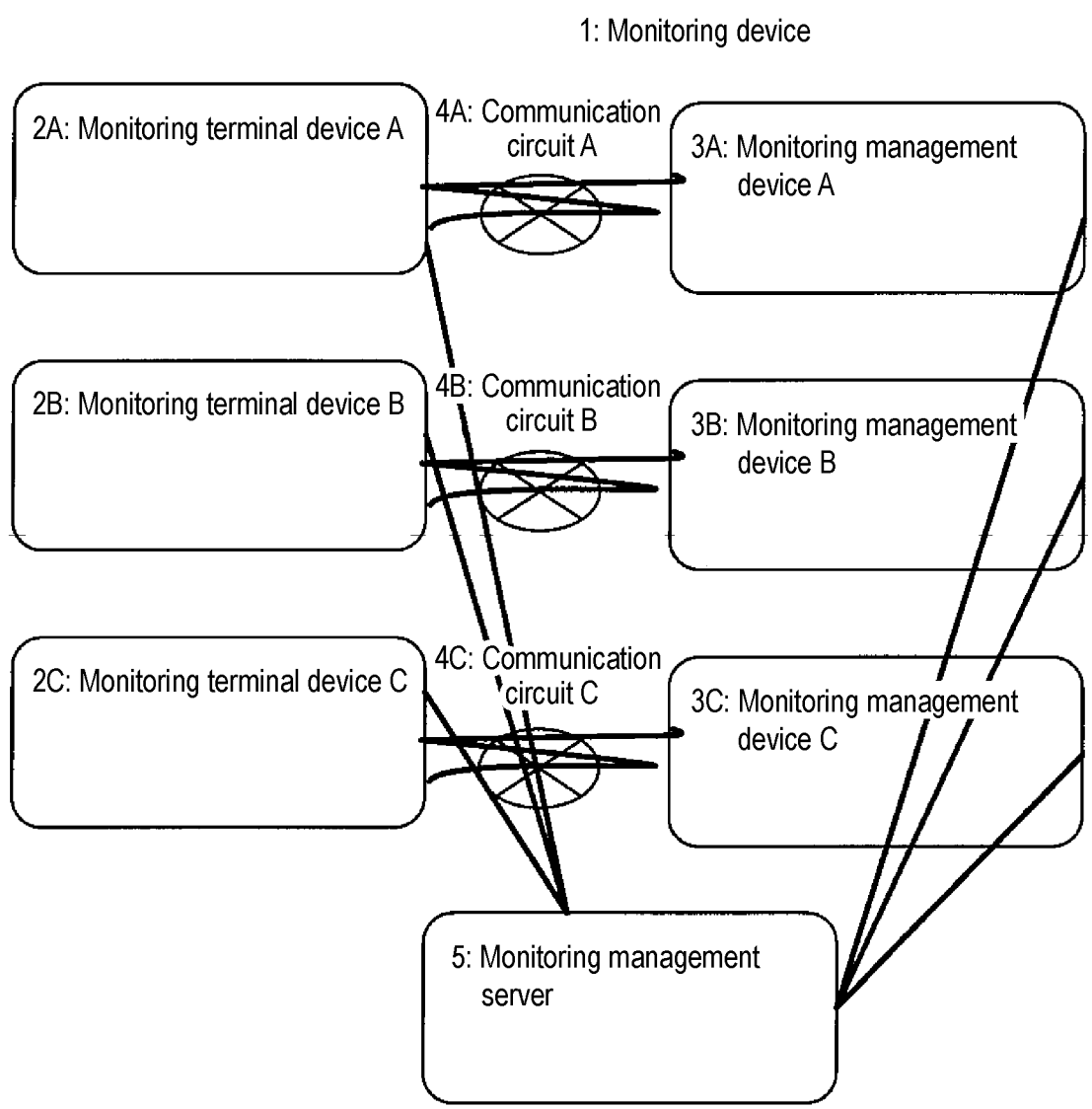
FIG. 4 is a functional block diagram illustrating the configuration of a monitoring device according to an embodiment.

FIG. 4 is a functional block diagram illustrating a configuration of the monitoring device according to an embodiment.

The monitoring device 1 includes monitoring terminal devices 2A to 2C, monitoring management devices 3A to 3C, and communication circuits 4A to 4C connecting the devices. A plurality of monitoring terminal devices may also be included. One and/or a plurality of monitoring management devices for managing a plurality of monitoring terminal devices may also be included. Further, a monitoring management server for managing a monitoring management device from an upper level may also be included.

The present invention encompasses any and all uses of the monitoring device of the present invention and is suitable for any application thereof, including methods using the monitoring device of the present invention and methods of using the same, methods of evaluating a ketogenic diet, methods of managing the ketogenic diet ingestion amount, and screening for animals for which a ketogenic diet feeding is effective.

While the embodiments of the present invention have been described, the present invention is not limited to the foregoing embodiments, and various design modifications may be made without departing from the effect of the present invention set forth in the claims.

REFERENCE SIGNS LIST

1 Monitoring device
2 Monitoring terminal device
2A Monitoring terminal device A
2B Monitoring terminal device B
2C Monitoring terminal device C
3 Monitoring management device
3A Monitoring management device A
3B Monitoring management device B
3C Monitoring management device C
4 Communication circuit
4A Communication circuit A
4B Communication circuit B
4C Communication circuit C
5 Monitoring management server

The invention claimed is:

1. A method of managing a ketogenic diet ingestion amount using a ketogenic diet monitoring device, the ketogenic diet monitoring device to improve a disorder comprising one or more of cardiovascular disorders, type 2 diabetes, epilepsy, acne, cancers, polycystic ovary syndrome, neurological disorders, Alzheimer's disease, Parkinson's disease, and head injury in a patient or pre-patient of the disorder against which ingestion of a ketogenic diet is effective including:

an ingestion information acquisition unit for acquiring information about an amount of ingestion of a ketogenic diet ingested into a body of the patient or pre-patient;

an acetone concentration measurement unit for measuring acetone concentration that is an amount of acetone in a gas carried from inside to outside of the body of the patient or pre-patient, a determination unit which, based on the information about the amount of ingestion of the ketogenic diet acquired by the ingestion information acquisition unit and the acetone concentration measured by the acetone concentration measurement unit, determines a state of metabolizing of the ketogenic diet by the patient or pre-patient, a determination accumulation unit for accumulating the determination by the determination unit; and a determination judgement unit for adjusting an amount of ingestion of the ketogenic diet of the patient or pre-patient based on the accumulated determination, the method comprising:

measuring the acetone concentration by the acetone concentration measurement unit;

calculating a rate of increase in the acetone concentration by the determination unit; and adjusting an amount of ingestion of the ketogenic diet of the patient or pre-patient according to the rate of increase in the acetone concentration by the determination judgement unit, wherein the measuring includes measuring the acetone concentration before and after ingestion of the ketogenic diet of the patient or pre-patient, the calculating includes calculating the rate of increase in the acetone concentration based on a difference in the acetone concentration before and after ingestion of the ketogenic diet, and the adjusting includes increasing the amount of ingestion of the ketogenic diet if the rate of increase in the acetone concentration exceeds a reference value set in advance, and decreasing the amount of ingestion of the ketogenic diet if the rate of increase in the acetone concentration does not exceed the reference value, and wherein the increasing or decreasing of the ketogenic diet is by only an appropriate amount of ingestion that is necessary and sufficient to improve the disorder in the patient or pre-patient while avoiding excessive ingestion of the ketogenic diet.

* * * * *